United States Patent [19]

Buren et al.

[11] 4,328,027

[45] May 4, 1982

[54] DI-TRIETHYLAMINE SALT OF N,N'-BIS-CARBOETHOXYMETHYL-N,N'-BIS-PHOSPHONOMETHYLUREA AND ITS USE AS A PLANT GROWTH REGULATOR

[75] Inventors: Lawrence L. Buren, Cupertino; George B. Large, Orinda, both of Calif.

[73] Assignee: Stauffer Chemical Company, Westport, Conn.

[21] Appl. No.: 254,836

[22] Filed: Apr. 16, 1981

[51] Int. Cl.$^3$ .......................... A01N 57/20; C07F 9/38
[52] U.S. Cl. ........................................ 71/86; 560/169; 260/938; 556/404
[58] Field of Search ............................ 560/169; 71/86

[56] References Cited

U.S. PATENT DOCUMENTS

| | | | |
|---|---|---|---|
| 3,257,479 | 6/1966 | Irani | 260/932 |
| 3,455,675 | 7/1969 | Irani | 71/86 |
| 3,556,762 | 1/1971 | Hamn | 71/86 |
| 3,714,067 | 1/1973 | King | 252/389 A |
| 3,763,281 | 10/1973 | Weil | 260/932 |
| 3,816,333 | 6/1974 | King | 252/389 A |
| 3,835,000 | 9/1974 | Frazier | 71/86 |
| 3,954,860 | 5/1976 | Birum | 71/86 |
| 4,191,552 | 3/1980 | Large | 560/169 |

*Primary Examiner*—Michael Shippen
*Attorney, Agent, or Firm*—Harry A. Pacini

[57] ABSTRACT

The di-triethylamine salt of N,N'-bis-carboethoxymethyl-N,N'-bis-phosphonomethylurea is disclosed herein, having utility in regulating the natural growth or development of plants.

3 Claims, No Drawings

DI-TRIETHYLAMINE SALT OF N,N'-BIS-CARBOETHOXYMETHYL-N,N'-BIS-PHOSPHONOMETHYLUREA AND ITS USE AS A PLANT GROWTH REGULATOR

BACKGROUND OF THE INVENTION

This invention is directed to a novel chemical compound and its use in regulating the natural growth or development of plants. In particular, this invention relates to the chemical treatment of plants to alter their natural growth or development for the purpose of enhancing various agricultural or horticultural features of the plants.

It is known that various features of plant growth can be modified or regulated to produce a variety of beneficial effects. For instance, defoliation can be achieved in such a manner as to inhibit leaf growth with no effect on productive plant parts. In fact, the latter often demonstrate extra growth as a result. As a further benefit, harvesting operations are facilitated. Defoliants are particularly useful in flax, cotton, and bean crops, and other crops of a similar nature. While defoliation results in the killing of leaves, it is not a herbicidal action since it does not harm the remainder of the plant. Indeed, killing of the treated plant is undesirable when defoliation is sought, since leaves will continue to adhere to a dead plant.

Another response demonstrated by plant growth regulants in the general retardation of vegetative growth. This response has a wide variety of beneficial features. In certain plants it causes a diminution or elimination of the normal apical dominance, leading to a shorter main stem and increased lateral branching. Smaller, bushier plants with increased resistance to drought and pest infestation are the result. Retardation of vegetative growth is also useful in turf grasses for lessening the vertical growth rate, enhancing root development, and producing a denser, sturdier turf. The retardation of turf grasses also serves to increase the interval between mowings of lawns, golf courses and similar grassy areas.

In many types of plants, such as silage crops, potatoes, sugar cane, beets, grapes, melons and fruit trees, the retardation of vegetative growth increases the carbohydrate content of the plants at harvest. it is believed that growth retardation or suppression at the appropriate stage of the development decreases the amount of carbohydrate available for vegetative growth and thereby enhances starch and/or sucrose content. Retardation of vegetative growth in fruit trees produces shorter branches and greater fullness of shape, and often results in lesser vertical elongation. These factors contribute to the ease of access of the ochard and simplify the fruit harvesting procedure.

BRIEF DESCRIPTION OF THE INVENTION

It has now been discovered that the di-triethylamine salt of N,N'-bis-carboethyoxymethyl-N,N'-bis-phosphonomethylurea is useful in regulating the natural growth or development of plants. This salt has the following formula:

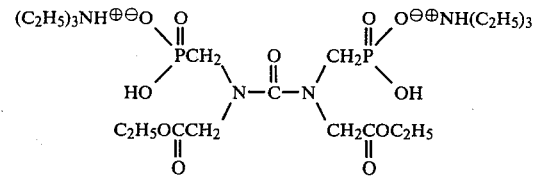

As employed herein, the term "natural growth or development" designates the normal life cycle of a plant in accordance with its genetics and environment, in the absence of artificial external influences. A preferred utility of the instant compounds is in increasing the sucrose yield of field grown sugarcane and sorghum. The term "regulating" is used herein to denote the bringing about through chemical means of any temporary or permanent modification or variation from the normal life cycle short of killing the plant. While these compounds can be applied in amounts sufficient to kill certain plants, it is contemplated herein to employ only such amounts as will serve to produce a regulating effect.

DETAILED DESCRIPTION OF THE INVENTION

In accordance with the instant invention, regulation of the natural growth or development of plants is achieved by the direct application of the above compound to the plants or to any of their above-ground portions at approximately 4 to 10 weeks prior to harvest. Application of the compound to the plant is achieved with a growth regulating effect, but without herbicidal results. As understood by those skilled in the art, amounts effective for this purpose vary, not only with the particular material selected for treatment, but also with the regulatory effect to be achieved, the species of plant being treated and its stage of development, and whether a permanent or transient regulating effect is sought. Other factors which may bear upon the determination of an appropriate plant regulating amount include the manner in which the treatment is to be applied, weather conditions such as temperature or rainfall, etc. The resulting regulation may arise from the effect of the chemical regulant on either the physiological processes of the plants or the morphology of the plant, or from both in combination or in sequence.

Morphological changes are generally noticeable by visual observation. Such changes occur in the size, shape, color or texture of the treated plant or any of its parts, as well as in the quantity of fruit or flowers the plant produces. Changes in the physiological processes, on the other hand, occur within the treated plant and are usually hidden from view. Changes of this type most often occur in the production, location, storage or use of chemicals naturally occurring in the plant, such as hormones. Physiological changes may be visually detectable when followed by a change in morphology. In addition, numerous analytical procedures for determining the nature and magnitude of changes in the various physiological processes are known to those skilled in the art.

The compound of the instant invention serves to regulate the natural growth or development of treated plants in a number of diverse ways, and it should be understood that the regulatory effects will vary from one plant species to the next or from one application rate to the next.

The compound is readily prepared from commercially available starting materials by procedures known in the art. The preparation is best understood by reference to Example 1 below. Examples 2 and 3 illustrate how the compound of the invention regulates the natural growth or development of plants. Although regulatory effects are often desirable in their own right, it is most often the ultimate result of these effects upon the economics of the crop which is of primary significance. Thus, increases in the yield of individual plants, increases in the yield per unit area, and reductions in the cost of harvesting and/or subsequent processing are all to be considered in assessing the consequence of an individual regulatory effect during the growth or development of a plant.

The examples which follow are presented as merely illustrative, non-limiting demonstrations of the preparation of the compound of the present invention and of its effectiveness in regulating the growth of plants.

EXAMPLE 1

This example illustrates the preparation of the compound of the present invention. The preparation is shown in four steps—the formation of N,N'-dicarboethoxymethylurea, the chloromethylation of the urea, the formation of the phosphonate ester by an Arbusov reaction with trimethylphosphite, and conversion of the phosphonate ester to the corresponding phosphonic acid which is subsequently neutralized with triethylamine.

Preparation of N,N'-Dicarboethoxymethylurea $$C_2H_5OCCH_2N=C=O + C_2H_5OCCH_2NH_2 \cdot HCl \xrightarrow[CHCl_3]{(C_2H_5)_3N}$$

$$C_2H_5OCCH_2NHCNHCH_2COC_2H_5 \quad 1.$$

A slurry was formed consisting of 12.9 grams (g) (0.1 mole) of carboethoxymethylisocyanate and 14.0 g (0.1 mole) of carboethoxymethylamine hydrochloride in 100 ml of chloroform. While the slurry was continuously stirred at room temperature, 10.1 g (0.1 mole) of triethylamine was added in dropwise manner. Stirring was continued for a total of thirty minutes at room temperature as the product formed a precipitate. The precipitate was filtered off, washed with water, and dried in an oven to yield 18.4 g of a white powder with melting point 141°–144° C. The structure as shown above was confirmed by mass spectrometry.

Preparation of N,N'-Bis-chloromethyl-N,N'-bis-carboethoxymethylurea

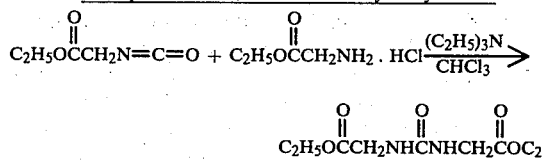

A reaction flask was charged with 100 cubic centimeters (cc) of chloroform, 18.4 g (0.079 mole) of N,N'-dicarboethoxymethylurea, and 6.0 g (0.2 mole) or paraformaldehyde. As the mixture was continuously stirred at room temperature, 23.6 g (14.3 cc, 0.2 mole) of thionyl chloride in a concentrated chloroform solution was added dropwise. A rise in temperature to 34° C. was observed. Hydrogen chloride and sulfur dioxide gases evolving from the reaction mixture were trapped in a caustic solution. The product was isolated by evaporation of the solvent, to produce 24.6 g of a yellow liquid, whose molecular structure was confirmed by infrared spectroscopy and nuclear magnetic resonance as that of the product shown above. The refractive index was $n_D{}^{30}=1.4764$.

Preparation of N,N'-Bis-carboethoxymethyl-N,N'-bis-(O,O-dimethyl-phosphonomethyl)urea

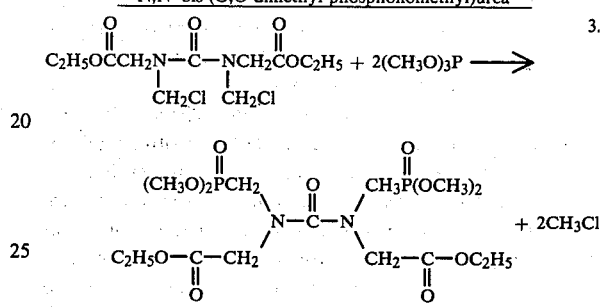

A reaction flask was charged with 20 g (0.061 mole) of N,N'-bis-carboethoxymethyl-N,N'-bis-chloromethylurea and 24.8 g (25 cc, 0.2 mole) of trimethylphosphite. After a mild rise in temperature, the reaction mixture was stirred for thirty minutes at room temperature, followed by one hour at 50° C. The product was isolated by evaporation to yield 25.5 g of a yellow liquid with refractive index $n_D{}^{30}=1.4672$. The structure shown above was confirmed by infrared spectroscopy and nuclear magnetic resonance.

Preparation of Di-triethylamine Salt of N,N'-Bis-carboethoxymethyl-N,N'-bis-phosphonomethylurea

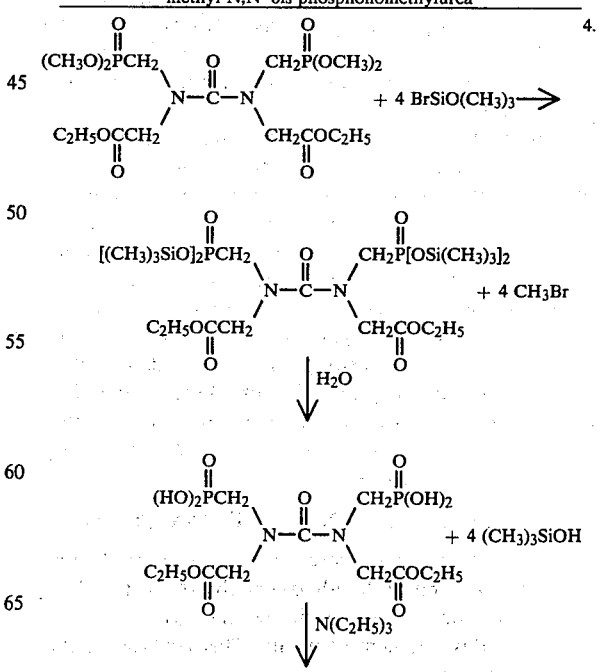

-continued
Preparation of Di-triethylamine Salt of N,N'-Bis-carboethoxy-methyl-N,N'-bis-phosphonomethylurea

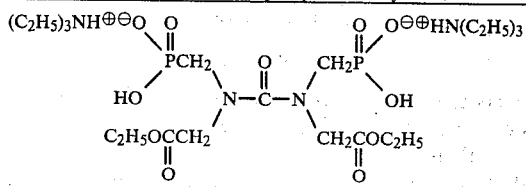

The phosphonate ester of the previous step (4.76 g, 0.01 mole) was placed under nitrogen and treated with 6.12 g (0.04 mole) or bromotrimethylsilane at 5° C. The mixture was stirred for one hour at room temperature, then poured into 300 ml of water and stirred for an additional thirty minutes. An organic layer 2 ml in volume separated, which was extracted with two portions of toluene followed by two portions of methylene chloride. The extracts were dried and stripped of solvent to yield 2–3 g of a white solid. The solid was then redissolved in toluene and excess triethylamine was added. The volatiles were then stripped off. The aqueous phase remaining from the extraction was then treated with excess triethylamine and extracted with toluene. The extract was dried and stripped, and the product combined with that taken from the original organic layer. Finally, the aqueous phase was itself stripped of water at a pressure of 1 mm mercury at 50° C. The total yield of all three products was 4.3 g of a solid with melting point 107°–115° C. The molecular structure of the product was confirmed as that shown above by nuclear magnetic resonance.

EXAMPLE 2

This example illustrates the utility of the compound of the present invention in regulating the growth of sweet sorghum (scientific name: *Sorghum volgare*).

The test procedure was as follows:

A series of white plastic pots, 7.5 inches (19.0 cm) in diameter, were filled with approximately 10 pounds (4.54 kilograms) each of sandy loam soil containing 100 parts per million (ppm) of cis-N-[(trichloromethyl)thio]-4-cyclohexene-1,2-dicarboximide (a commercially available fungicide) and 150 ppm of 17-17-17 fertilizer (i.e., comprising 17% by weight each of N, $P_2O_5$, and $K_2O$). Eight sorghum seeds were placed in each pot and the pots were placed in a greenhouse in which the temperature was maintained at 27° C. during the day and 21° C. at night. During the next five weeks, the emerging plants were thinned down to one per pot. The pots were fertilized periodically with 17-17-17 fertilizer.

Approximately two weeks prior to the emergence of the seedheads (eleven weeks after seeding), the plants were sprayed with a solution consisting of the test compound dissolved in equal proportions of acetone and water. The spraying system was pressurized by carbon dioxide and mounted on a bicycle-type apparatus. The test solution was sprayed at a rate of 80 gallons per acre (750 liters per hectare). The concentration of the solution was pre-determined to produce an application rate of 8 pounds of the test compound per acre when sprayed over the pots at a total solution volume of 80 gallons per acre.

Following treatment, the plants were placed in the greenhouse for an additional four weeks. During this time, the degree of seedhead emergence and pollen shedding were recorded periodically.

Approximately fifteen weeks after the seeds were planted, the plants were harvested. The stalks were cut at soil level and the seedhead and peduncle were removed. For each stalk, the seedhead was weighed (fresh weight), then dried and re-weighed (dry weight), and the peduncle length was measured. The number of side shoots on each plant was recorded, and the shoots were then stripped from the stalk and weighed. Next, the length and width of each stalk were determined. Each stalk was then chopped into small segments and squeezed in a hydraulic press at a pressure of 20,000 pounds per square inch (13,800 Newtons per square centimeter). The quantity of the expressed juice was measured as well as its quality in terms of total dissolved solids. The latter was measured with a hand juice refractometer, and is expressed as weight percent of the juice.

Four replications were performed on the test compound. In addition, four untreated plants were included as check plants for comparison. The results are shown in Tables I and II.

Table I lists the data pertaining to seedhead emergence and pollen shedding. The data listed are averages of each set of four replications. It is clear in each case that the extent of seedhead emergence and pollen shedding was reduced when the test compounds were applied. This reduction in flowering is one indication of an increase in the efficiency of sucrose production and storage.

Table II lists averages of the measurements taken on the seedhead, peduncle, stalk, expressed juice and side shoots after the harvesting of the plants. The data indicates a reduction in seedhead fresh and dry weights, peduncle length, and stalk height, and an increase in the percentage of total dissolved solids in the expressed juice as a result of the test compound.

TABLE I
FLOWERING DATA
Test Compound:

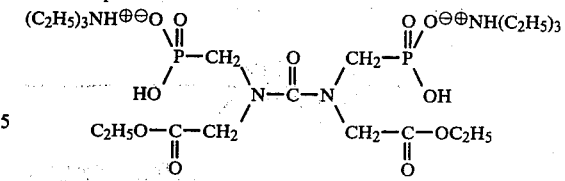

Application Rate: 8 lb/A

| Days After Treatment | Seedhead Emergence (%)* | | Pollen Shedding (%)* | |
|---|---|---|---|---|
|  | Test | Check | Test | Check |
| 6 | 10 | 8 | 8 | 5 |
| 8 | 10 | 45 | 10 | 38 |
| 10 | 10 | 63 | 10 | 59 |
| 13 | 10 | 73 | 10 | 66 |
| 17 | 10 | 73 | 10 | 66 |

*Each figure represents the average of 4 replications.

TABLE II
HARVEST DATA
Test Compound and Application Rate: same as Table I

|  | Treated Plants* (8 lb/A) | Check Plants* |
|---|---|---|
| Peduncle Length (mm) | 60 | 202 |
| Stalk: |  |  |
|   Height (mm) | 848 | 904 |
|   Weight (g) | 114 | 112 |
| Expressed Juice: |  |  |
|   Quantity (ml) | 32 | 40 |

TABLE II-continued

HARVEST DATA

Test Compound and Application Rate: same as Table I

| | Treated Plants* (8 lb/A) | Check Plants* |
|---|---|---|
| Total Dissolved Solids (wt %) | 16.3 | 13.9 |
| Seedhead Weight: | | |
| Fresh (g) | 12.3 | 28.1 |
| Dried (g) | 4.5 | 9.2 |
| Side Shoots: | | |
| Number | 7 | 1 |
| Fresh Weight (g) | 59 | 31 |

*Each figure represents the average of 4 replications.

EXAMPLE 3

This example offers test results obtained at lower application rates.

The procedure was the same as that used for Example 1, except that treatment of the plants occurred nine weeks and two days after seeding, and harvesting occurred from four weeks and three days to five weeks later. Two application rates of the test compound was used—2 lb/A and 4 lb/A—and the concentrations of the spray solutions were adjusted accordingly.

The results are shown in Tables III and IV, where the same type of effect is observed as is observed in Tables I and II, the more pronounced effect occurring at 4 lb/A.

TABLE III

FLOWERING DATA

Test Compound: same as Table I
Application Rates: 2 and 4 lb/A, as shown

Application Rates (lb/A):

| Days After Treatment | Seedhead Emergence (%) | | | Pollen Shedding (%) | | |
|---|---|---|---|---|---|---|
| | 0 | 2 | 4 | 0 | 2 | 4 |
| 17 | 70 | 58 | 3 | 47 | 20 | 0 |
| 19 | 85 | 90 | 38 | 73 | 68 | 8 |
| 21 | 88 | 97 | 57 | 82 | 84 | 21 |
| 24 | 100 | 100 | 98 | 100 | 98 | 90 |

Each figure represents the average of 6 replications.

TABLE IV

HARVEST DATA

Test Compound: same as Table I
Application Rates: 2 and 4 lb/A, as shown

| | Check Plants* | Treated Plants* | |
|---|---|---|---|
| | | 2 lb/A | 4 lb/A |
| Penduncle Length (mm) | 336 | 323 | 242 |
| Stalk: | | | |
| Height (mm) | 1728 | 1660 | 1559 |
| Weight (g) | 352 | 343 | 358 |
| Expressed Juice: | | | |
| Quantity (ml) | 141 | 146 | 137 |
| Total Dissolved Solids (wt %) | 114.4 | 12.3 | 12.6 |
| Seedhead Weight: | | | |
| Fresh (g) | 75 | 69 | 44 |
| Dried (g) | 35 | 29 | 16 |

*Each figure represents the average of 6 replications.

METHODS OF APPLICATION

The compound of the present invention is most useful when applied directly to the plants subsequent to their emergence from the soil. When applied in such a manner, the compound is generally embodied in formulations suitable for convenient application. Typical formulations contain additional ingredients or diluent carriers which are either inert or active. Examples of such ingredients or carriers are water, organic solvents, oil and water, water-oil emulsions, wetting agents, dispersing agents, and emulsifying agents. The formulations generally take the form of dusts, solutions, emulsifiable concentrates, or wettable powders.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease in incorporation some liquid nonionic agents are also suitable in the dust formulations.

Preferred dust carriers are micaceous talcs, pyrophyllite, dense kaolin clays, tobacco dust and ground calcium phosphate rock.

Preferred grinding acids are attapulgite clay, diatomaceous silica, synthetic fine silica and synthetic calcium and magnesium silicates.

Most preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and diteritary acetylenic glycols. Preferred dispersants and methyl cellulose, polyvinyl, alcohol, lignin sulfonates, polymeric alkylnaphthalene sulfonates, sodium naphthalene- sulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anti-caking and antistatic agents. The particle size of the carrier is usually in the range of 30 to 50 microns.

B. SOLUTIONS

Liquid solutions are the preferred formulations for the purposes of the instant invention. Water is the preferred carrier. The active compound is dissolved in water such that application at the rate of about 1 to about 200 gallons of solutions per acre (about 9 to about 1875 liters per hectare) will provide the required amount of active ingredient.

Typical solutions for such use also contain a small amount of non-phytotoxic surfactant to improve the wetting ability of the solution and thus its distribution over the plant surface. The surfactant is normally used in an amount ranging from about 0.01% by weight to about 5% by weight with respect to the water, preferably from about 0.05% by weight to about 0.5% by weight.

The surfactants for use as described above can be anionic, cationic, nonionic, ampholytic and zwitterionic types.

Examples of suitable anionic surfactants for use herein are the alkali metal (for example, sodium) ammonium and amine salts of fatty alcohol sulfates having from 8-18 carbon atoms in the fatty chain and sodium salts of alkyl benzene sulfonates having from 9 to 15 carbon atoms in the alkyl chain.

Examples of suitable cationic surfactants are dimethyl dialkyl quaternary ammonium salts wherein the alkyl chains contain from about 8 to 18 carbon atoms and the salt-forming anion is a halogen.

Examples of suitable nonionic surfactants are the polyoxyethylene adducts of fatty alcohols having 10 to 18 carbon atoms, and the polyethylene oxide condensates of alkyl phenols wherein the alkyl chain contains from about 6 to 12 carbon atoms and the amount of ethylene oxide condensed onto each mole of alkyl phenol is from about 5 to 25 moles, and the polyethylene oxide condensates of sorbitan esters wherein the amount of ethylene oxide condensed onto each mole of sorbitan ester is about 10 to 40 moles.

Examples of suitable ampholytic surfactants are derivatives of aliphatic secondary or tertiary amines in which one of the aliphatic substituents contain from about 8 to 18 carbon atoms and one contains an anionic water solubilizing group, e.g., sulfate or sulfonate. Specific suitable ampholytic surfactants are sodium-3-dodecylaminopropionate and sodium-3-dodecyl amino propane sulfonate.

Examples of suitable zwitterionic surfactants are derivatives of aliphatic quaternary ammonium compounds in which one of the aliphatic constituents contains from about 8 to 18 carbon atoms and one contains an anionic water solubilizing group. Specific examples of zwitterionic surfactants are 3-(N,N-dimethyl-N-hexadecylammonio)propane-1-sulfonate and 3-(N,N-dimethyl-N-hexadecylammonio)-2-hydroxy propane-1-sulfonate.

C. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably, mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

D. WETTABLE POWDERS

Wettable powders are water-dispersible compositions containing the active material, an inert solid extender, and one or more surfactants to provide rapid wetting and prevent heavy flocculation when suspended in water.

The inert solid extenders are usually of mineral origin such as the natural clays, diatomaceous earth and synthetic minerals derived from silica and the like. Examples of such extenders include kaolinites, attapulgite clay, montmorillonite clays, synthetic silicas, synthetic magnesium silicate and calcium sulfate dihydrate.

Suitable surfactants for use in such compositions include both the nonionic and anionic types, and those most suitable for the preparation of the dry, wettable products of this invention are solid forms of compounds known to the art as wetters and dispersants. Occasionally a liquid, nonionic compound classified primarily as an emulsifier may serve as both wetter and dispersant.

Most preferred wetting agents are alkylbenzene and alkynaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohols, lignin sulfonates, polymeric alkylnaphthalene sulfonates, sodium naphthalenesulfonate, polymethylene bisnaphthalenesulfonate, and sodium-N-methyl-N-(long chain acid) taurates.

Wetting and dispersing agents are usually present at concentrations of from about 0.5 weight percent to 5 weight percent. The inert extender then completes the formulation. Where needed, 0.1 weight percent to 1.0 weight percent of the extender may be replaced by a corrosion inhibitor or an antifoaming agent or both.

Thus, wettable powder formulations will contain from about 25 to 90 weight percent active material, from 0.5 to 2.0 weight percent wetting agent, from 0.25 to 5.0 weight percent dispersant, and from 9.25 to 74.25 weight percent inert extender. When the wettable powder contains a corrosion inhibitor or an antifoaming agent, the former will generally comprise about 1 percent or less of the composition and the latter about 0.5 percent or less, on a weight basis.

E. IN GENERAL

In general, any conventional method of application can be used. Dusts and liquid compositions can be applied by the use of powder dusters, boom and hand sprayers, and spray dusters. The compositions can also be applied from airplanes as dusts or sprays because they are effective in very low dosages.

Compositions containing the compound of the present invention can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the active compound in the irrigation water will range from about 10 to 150 parts per million by weight. The irrigation water is preferably applied by the use of sprinkler systems. Such application is most effectively done about 4 to 10 weeks prior to harvest.

The amount of composition of the present invention which constitutes an effective, plant-regulating, non-lethal amount depends upon the nature of the plants to be controlled. The rate of application of the active ingredient varies from about 0.1 to about 20 pounds per acre (lb/A) (0.11 to 22 kilograms per hectare, kg/ha), preferably about 0.1 to about 10 lb/A (0.11 to 11 kg/ha), most preferably about 0.5 to about 8 lb/A (0.56 to 9.0 kg/ha), with the actual amount used depending on the overall cost and the desired results.

What is claimed is:

1. A compound having the formula

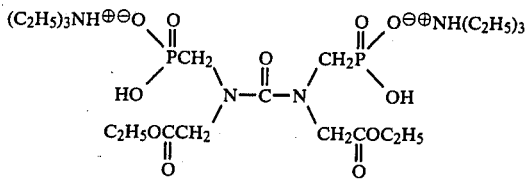

2. A biologically active composition comprising (a) an effective, plant-regulating, non-lethal amount of a compound having the formula

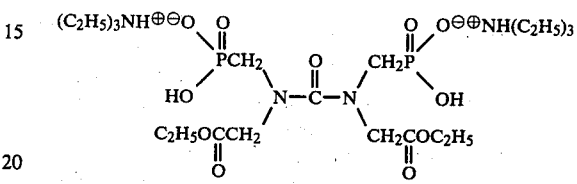

and (b) an inert diluent carrier.

3. A method of regulating the natural growth or development of plants which comprises applying to said plants a biologically active composition comprising (a) an effective, plant-regulating, non-lethal amount of a compound having the formula

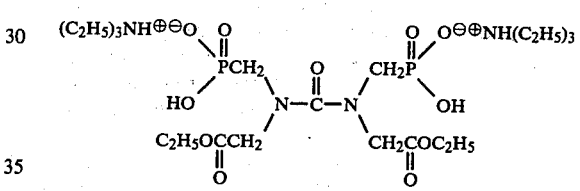

and (b) an inert diluent carrier.

* * * * *